(12) United States Patent
Sen et al.

(10) Patent No.: US 6,932,981 B2
(45) Date of Patent: Aug. 23, 2005

(54) RAPIDLY DISINTEGRATING SUSTAINED RELEASE CEFUROXIME AXETIL COMPOSITION

(75) Inventors: Himadri Sen, Aurangabad (IN); Rajesh Suresh Kshirsagar, Aurangabad (IN); Anupa Ramesh Menjoge, Aurangabad (IN)

(73) Assignee: Lupin Laboratories, Ltd., Maharashtra (IN)

( * ) Notice: Subject to any disclaimer, the term of this patent is extended or adjusted under 35 U.S.C. 154(b) by 0 days.

(21) Appl. No.: 09/928,466

(22) Filed: Aug. 13, 2001

(65) Prior Publication Data

US 2002/0119195 A1 Aug. 29, 2002

Related U.S. Application Data

(63) Continuation-in-part of application No. 09/702,042, filed on Oct. 30, 2000.

(51) Int. Cl.$^7$ .................................................. A61K 9/20
(52) U.S. Cl. .................. 424/464; 424/462; 424/468; 424/474; 424/482; 514/772.1; 514/772.4
(58) Field of Search .................................... 424/462, 464, 424/468, 474, 482; 514/772.1, 772.4, 226.8

(56) References Cited

U.S. PATENT DOCUMENTS 4,325,960 A * 4/1982 Godfredsen et al. ........ 424/270
5,580,578 A * 12/1996 Oshlack et al. ............. 424/468
6,372,255 B1 * 4/2002 Saslawski et al. .......... 424/473

FOREIGN PATENT DOCUMENTS

| DE | 19835823 | 10/1999 |
| EP | 0280571 | 8/1988 |
| WO | 9324109 | 12/1993 |
| WO | WO 99/44614 | * 9/1999 |
| WO | 0076479 | 12/2000 |

* cited by examiner

Primary Examiner—Thurman K. Page
Assistant Examiner—Lakshmi Channavajjala
(74) Attorney, Agent, or Firm—Ladas & Parry LLP (57) ABSTRACT

A fast disintegrating controlled release oral composition comprising a core material containing cefuroxime axetil present as controlled release form, the cefuroxime axetil being provided with an outer coating of a copolymer selected from aqueous dispersions of enteric methacrylic acid and methacrylic acid esters anionic copolymers having carboxyl group as the functional group or mixtures thereof and an inner coating of a sustained-release copolymer selected from aqueous dispersions of acrylate and methacrylate pH independent copolymers having quaternary ammonium group as a functional group or mixtures thereof, and optionally probenecid. Additionally, the coating composition may contain plasticizers. The composition is suitable for once daily administration.

64 Claims, 3 Drawing Sheets

Plot of % release of cefuroxime V/s time with use of Eudragit polymers alone or in combination.

Figure 1- Plot of % release of cefuroxime V/s time with use of Eudragit polymers alone or in combination.

Figure-1

Figure 2- Linear plot of mean serum concentrations V/s time for controlled release (cefuroxime 1 g +immediate release probenecid 1g) tablets

Figure- 2

Figure 3- Linear plot of mean serum concentration V/s time for controlled release cefuroxime (1 g) tablets without probenecid

Figure- 3

RAPIDLY DISINTEGRATING SUSTAINED RELEASE CEFUROXIME AXETIL COMPOSITION

This application is a continuation in part of application Ser. No. 09/702,042, filed Oct. 30, 2000.

FIELD OF THE INVENTION

This invention relates to a fast disintegrating, sustained controlled release cefuroxime axetil oral composition. More particularly, the invention relates to controlled release granules of cefuroxime axetil suitable for once daily administration.

BACKGROUND OF THE INVENTION

Most drugs used to treat microbial infections are given more than once during a dosage regimen. The objectives during antimicrobial therapy are to maximize blood concentration, preferably several fold higher than the minimum inhibitory concentration (MIC) for the particular agent, but to minimize both the risk of toxicity to the patient and of promoting microbial resistance. Although oral administration will be the preferred route, in the case of antibiotics this route is frequently unattractive because of their low or variable oral bioavailability. In addition extremely high plasma concentrations of antibiotics are frequently required to achieve their MIC values towards certain gram-negative bacteria. (Antibiotic and Chemotherapy: Anti-infective agents and their use in therapy, $7^{th}$ edition, Ed. by O'grady F., Finch R. G., Lambert H. P., Greenwood D.; Churchill Livingstone, 1997).

While many compounds are known to be useful as pharmacologically active substances, some of them have relatively short biological half-life and need to be administered several times a day in order to achieve desired therapeutic effect. However, a decrease in the frequency of administration will not only reduce the burden on the patient but will also increase compliance and thus provide greater therapeutic effect. It can be achieved by controlling the release of active ingredients, so that the effective level is maintained in the blood for a prolonged period of time or by reducing the elimination of the active from the body thereby increasing its concentration in blood resulting in its retention in blood for longer period.

This has been primarily achieved by development of new drug delivery systems utilizing diverse techniques and principles. Amongst these, known in the art is one such delivery system, which employs the use of pH dependent and pH independent polymers. The present invention uses a combination of methacrylic acid copolymers wherein one controls the release of the drug in acidic media and the polymers, which are essentially pH independent control the release at later stage. Control of the rate of release can produce constant blood levels of the active ingredient that may result in reducing the frequency of administration, thereby improving patient compliance to the dosage regimen.

Many drugs and drug metabolites are actively secreted by the proximal tubular active transport mechanism and interactions may arise from competition for these systems. Particularly with antibiotic therapy, active tubular secretion is a significant route of elimination. Drugs that use the same active transport system in the kidney tubules can compete with one another for secretion. Probenecid belongs to this class of drugs, which is able to compete successfully with some other drugs for an active secretion mechanism in the kidney tubule. This prevents them from being secreted into the tubular filtrate. Probenecid is later passively reabsorbed from the kidney tubules. Probenecid was extremely useful in the early days of penicillin when the combination raised and prolonged penicillin plasma levels. Inhibition of the urinary excretion of penicillin and some cephalosporins has been used as a device to increase the biliary excretion of these agents, thereby raising the antibiotic concentrations in the biliary tract. This has been used to improve the efficacy of antibiotic treatment (Antibiotic and Chemotherapy: Anti-infective agents and their use in therapy, $7^{th}$ edition, Ed. by O'grady F., Finch R. G., Lambert H. P., Greenwood D.; Churchill Livingstone, 1997).

Cefuroxime, as disclosed in British Patent No. 1453049, is a valuable broad spectrum antibiotic characterized by high activity against a wide range of gram-positive and gram-negative microorganisms. Antibiotics for oral administration should be in a form which provides high bioavailability, whereby absorption into the blood from the gastro-intestinal tract (GIT) is maximized. However, when cefuroxime is administered orally, it is poorly absorbed in the GIT hence it is administered parenterally.

U.S. Pat. No. 4,267,320 discloses that esterification of carboxyl group of cefuroxime to 1-acetoxyethyl ester i.e. cefuroxime axetil enhances absorption of cefuroxime from GIT where upon esterifying group is hydrolysed by enzymes present in human body.

Pure cefuroxime axetil can be produced in crystalline form or amorphous form. U.S. Pat. No. 4,820,833 discloses that amorphous cefuroxime axetil is more stable with increased absorption via GIT and has a correspondingly high level of bioavailabilty on oral or rectal administration.

U.S. Pat. No. 4,897,270 discloses a film coated cefuroxime axetil tablet to mask the bitter taste of the active upon oral administration. The patent teaches that conventional film coated tablets result in low levels of absorption of cefuroxime axetil from GIT and this is overcome by control of the film coat rupture time and use of a tablet core which disintegrates immediately following rupture of the film coat. The patent further teaches that cefuroxime axetil once in contact with aqueous media can form a gelatinous mass. This gelling effect is temperature dependent but does occur at temperatures of about 37° C., i.e. at the physiological temperature at which the disintegration of orally administered tablets takes place. The relatively slow permeation of moisture from the film coat to the core, which occurs upon administration of the tablets provided with conventional film coats leads to gelling of cefuroxime axetil present in the core. The gel formation leads to poor disintegration of the tablet core and hence to poor dissolution of cefuroxime axetil, thus the absorption from the GIT is greatly reduced. This occurs with both the crystalline and amorphous form of cefuroxime axetil.

However, Patent Application No. WO 99/44614 criticizes that such thin film coating with the water soluble film-forming material cannot completely block the absorption of moisture into the core upon long term storage and thus rather may cause gelation of the active ingredient within the core of the tablet upon storage.

As an effort to prevent the gelation of the cefuroxime axetil particles, U.S. Pat. No. 4,865,851 discloses cefuroxime axetil composition comprising particulate cefuroxime axetil coated with an integral coating of a lipid or mixture of lipids which are insoluble in water and which serves to mask the bitter taste of cefuroxime axetil but disperses or dissolves on contact with gastro-intestinal fluid.

The resulting particles can be incorporated into pharmaceutical compositions for oral administration, for example aqueous suspension, dry product for reconstitution with water or granules. However, the drawback is that coated particles having diameter of less than 250 microns are preferred and the coating procedure employed is rather elaborate, resulting in the process, which is inconvenient for preparing solid dosage forms of cefuroxime axetil for oral administration.

Patent Application No. WO 99/44614 discloses a pharmaceutical composition containing cefuroxime axetil, which is not gelled by moisture absorption and is thus stable during storage period comprising amorphous cefuroxime axetil and silicon dioxide or its hydrate as a microenvironmental pH adjustor and an anti-gelling agent for cefuroxime axetil.

Patent Application No. WO 99/08683 discloses a pharmaceutical composition comprising of a co-precipitate of cefuroxime axetil and a water-soluble excipient selected from the group consisting of povidone, hydroxy propyl cellulose, methylcellulose, lactose, mannitol and sorbitol. The co-precipitate is made by dissolving the active ingredient and the water-soluble excipient in a solvent or combination of solvents and evaporating the solvents. The solvents in which cefuroxime axetil and the excipient having relatively high solubility have been used so as to minimize the amount of solvent used.

Patent Application No. WO 99/62559 discloses a pharmaceutical tablet comprising cefuroxime axetil and a carbonate or a bicarbonate to enhance the rate of disintegration of the tablets in gastric fluid.

Patent Application No. WO 00/30647 discloses cefuroxime axetil in non-gelatinous form on contact with an aqueous liquid comprising cefuroxime axetil in the form of a solid solution in a polymer or in the form of a solid dispersion on an adsorbent, useful for pharmaceutical composition.

U.S. Pat. No. 5,580,578 discloses a stable solid controlled release formulation comprising an active coated with a plasticized aqueous dispersion of a hydrophobic acrylic polymer. The coated substrate is cured at a temperature greater than the glass transition temperature of the acrylic polymer used, for 24 to 60 hours to provide a stabilized dissolution of the active which is unchanged after exposure to accelerated storage conditions.

U.S. Pat. No. 5,578,316 discloses a taste masked pharmaceutical granular composition comprising a core material containing an unpleasant tasting drug having coatings of separate layers of aqueous dispersions of methacrylate ester copolymers providing an immediate release of the drug in the stomach.

As none of the prior arts summarized above provide a controlled release cefuroxime axetil composition, a need exists for such a composition wherein the active ingredient, cefuroxime axetil is released in a controlled manner maintaining therapeutically effective level in the blood such that the composition is suitable for once-daily administration thereby improving patient compliance to the dosage regimen.

Thus the object of the present invention is to provide a long acting pharmaceutical composition comprising controlled release cefuroxime axetil wherefrom the cefuroxime axetil is released in a manner such that the composition is suitable for once daily administration.

Another object is directed to controlling the release profile of the active ingredient, cefuroxime from the delivery system and thereby maintaining the blood levels for longer duration or controlling the release profile of the active coupled with use of selective adjuvant which would reduce the elimination/excretion of the active ingredient from the body for further prolonging the blood levels to improve the efficacy of the composition.

Another object is directed to provide for a controlled release and formulation of cefuroxime axetil with maximum bactericidal activity and also provide desired serum levels that would continuously exceed the MIC of the pathogen and favour providing optimal dosing regimen.

Yet further object is directed to provide for a controlled release formulation of cefuroxime axetil which would enable continuously maintaining concentrations above a certain level related to the MIC for the specific pathogen and thus would be more efficacious than the high peak and trough concentrations obtained with an intermittent dosing regimen.

Further object of the present invention thus directed to provide a long acting pharmaceutical composition suitable for once daily administration comprising controlled release cefuroxime axetil optionally in combination with immediate release or controlled release probenecid, which would release cefuroxime axetil in a manner such that effective blood levels of cefuroxime are maintained for longer duration and elimination/excretion of cefuroxime from body is reduced by use of probenecid as an adjuvant thereby further extending effective blood levels of cefuroxime.

Yet further object of the present invention also aims at overcoming the limitation of gelling tendency of cefuroxime axetil by rapid disintegration of the tablet and still controlling the release of the drug by particulate coating whereby the composition would disintegrate in the stomach on contact with gastrointestinal fluid resulting in coated controlled-release granules with selective coating to release the active drug slowly over a desired period of time thus sustaining its therapeutic action.

SUMMARY OF THE INVENTION

Thus according to the basic aspect of the present invention there is provided a fast disintegrating controlled release oral composition comprising a core material containing cefuroxime axetil present as controlled release form, and optionally probenecid, said controlled release form comprising:

a) an outer coating of a copolymer selected from aqueous dispersions of enteric methacrylic acid and methacrylic acid esters anionic copolymers having carboxyl group as the functional group or mixtures thereof and;

b) an inner coating of a sustained-release copolymer selected from aqueous dispersions of acrylate and methacrylate pH independent, neutral copolymers having quaternary ammonium group as a functional group or mixtures thereof.

The composition of the present invention rapidly disintegrates into controlled release cefuroxime axetil granules. The controlled release is obtained by coating the cefuroxime axetil core material with aqueous dispersions of methacrylic acid copolymers. The formulation is so provided that the gelling of cefuroxime axetil when in contact with aqueous media is overcome at the same time controlled release of cefuroxime axetil is achieved and probenecid helps in reducing the elimination rate of cefuroxime to provide long lasting blood levels. In addition, the composition further comprises, one or more of a water soluble and/or water dispersible diluent wherein the quantities of methacrylic acid copolymers and diluents are such that cefuroxime axetil is released at a rate suitable for once daily administration of the pharmaceutical composition.

The composition of the present invention disintegrate fast thereby avoiding gelling of the drug and yet provide controlled release of cefuroxime axetil over sustained period. The coated granules release the drug in a controlled manner. The therapeutically effective blood levels of the drug can be prolonged further by using probenecid as an antibiotic adjuvant. The following are the salient features of the compositions of present invention which provide the desired once daily composition of cefuroxime axetil i) fast disintegration of the composition to avoid gelling of cefuroxime axetil ii) coated controlled release granules having more than one coat, resulting after disintegration of composition providing sustained-release over time iii) the outer enteric polymeric coat controls the initial rapid release of the drug in acidic environment iv) the inner polymeric coat of pH independent polymers controlling the release of the drug thereafter v) optional use of probenecid as antibiotic adjuvant to reduce the elimination rate of cefuroxime and hence providing longer lasting blood levels.

The excretion of the cephalosporins or other betalactam antibiotics which are excreted by renal tubular secretion is reduced when given concurrently with probenecid resulting in increased and prolonged antibiotic serum concentration and prolonged half life.

Since the antibiotics are high dosing/high frequency, extended release drug delivery systems have not been very successful in reducing the frequency of dosing. In the present invention once a day administration of cefuroxime axetil is achieved either by controlling the release by coating with methacrylate polymers or by combination of controlling the release and use of the selective adjuvant, probencid to prolong the elimination of cefuroxime from the body.

According to another aspect the present invention provides a process for preparing a fast disintegrating controlled release oral composition containing cefuroxime axetil as controlled release form, which comprises spraying onto a fluidized bed of cefuroxime axetil core material an aqueous dispersion of an inner polymeric coating, retrieving and drying the coated core material and applying to a fluidized bed of the dried material an aqueous dispersion of an outer polymeric coating material and drying the coated particles.

According to another aspect the present invention provides for various forms of said fast disintegrating controlled release oral composition of cefuroxime axetil in the form of monolithic tablets or bilayered tablets following anyone of the processes hereunder:

i) Comprising mixing together cefuroxime axetil, diluents and wetting agent to form a blend, further compacting or wet granulating, sizing and coating the granules by wet granulation or coating in fluidized bed processor using copolymers a) and b), further drying, sizing, lubricating the granules and compressing to form monolithic tablets or bilayered tablets.

ii) Comprising mixing together cefuroxime axetil, diluents and wetting agent to form a blend, further compacting or wet granulating, sizing and coating the granules by wet granulation or coating in fluidized bed processor using copolymers a) and b), further drying, sizing, lubricating the granules and compressing into tablets along with immediate release probenecid granules to form monolithic tablets or bilayered tablets.

iii) Comprising mixing together probenecid, diluent and disintegrant together, compacting or wet granulating, sizing and coating the granules by wet granulation or coating in fluidized bed processor using copolymers a) and b), further drying, sizing, lubricating the granules and compressing into tablets along with coated controlled release cefuroxime axetil granules to form monolithic tablets or bilayered tablets.

iv) Comprising mixing together probenecid, diluent and disintegrant together, compacting or wet granulating, sizing and blending with lubricant and compressing the blend into tablets along with controlled release coated granules of cefuroxime axetil to form monolithic tablets or bilayered tablets.

The effective therapeutic once daily dose of the cefuroxime that can be administered by compositions of present invention is 1.0 g cefuroxime alone or 1.0 g cefuroxime and 1.0 g probenecid.

DETAILED DESCRIPTION OF THE COMPOSITION

The composition of this invention is in the form of a fast disintegrating tablet yet providing controlled release comprising cefuroxime axetil, methacrylic acid copolymers, water soluble and/or water dispersible diluents, suitable disintegrants, pharmaceutically acceptable tablet excipients, and optionally probenecid.

The present invention is achieved either by controlling the release of cefuroxime axetil or by combination of controlling the release and reducing its elimination from the body to achieve long lasting blood levels.

The pharmaceutical composition of the present invention comprises of cefuroxime axetil granules coated with methacrylic acid copolymers as controlled release form, optionally in combination with controlled release or immediate release probenecid. The controlled release coatings are derived from aqueous dispersions of methacrylic acid copolymers. The use of coated cefuroxime axetil further extends its elimination from the body.

Examples of other cephalosporin antibiotics which may be used include cephalexin, cefaclor, cefamandole, cefoxitin, cephalothin, moxalactam, cephapirin, ceftizoxime, cefonicid and, pharmaceutically acceptable hydrates, salts or esters thereof. Examples of other betalactam antibiotics, which may be used are amoxicillin, ampicillin, and cloxacillin. The invention may be useful for an active ingredient, which has a tendency to gel on contact with aqueous media.

The probenecid may be used as an antibiotic adjuvant for reducing the elimination rate and increasing the half-life of the therapeutically active ingredient, cefuroxime.

According to present invention the pharmaceutical composition contains cefuroxime axetil in an amount from about 30% to about 80% by weight of controlled release form.

Further, the cefuroxime axetil may be present in an amount from 250 mg to 1000 mg per tablet.

Eudragit L and S comprise acrylic/methacrylic acid anionic copolymers with carboxyl groups, whereby they become soluble above pH 5.5 and 7.0 respectively.

More precisely, Eudragit L is a poly(methacrylic acid, methyl methacrylate) with a molar ratio of 1:1 and a molecular weight of 135,000 or a poly(ethyl acrylate, methacrylic acid) with a molar ratio of the monomeric units of 1:1 and a molecular weight of 250,000. Eudragit S is a poly(methacrylic acid, methyl methacrylate) with a molar ratio of the monomeric units of 1:2 and a molecular weight of 135,000.

Eudragit RS and RL are insoluble but swellable acrylic/methacrylic acid neutral copolymers with quaternary ammonium groups present as chlorides, which completely dissociate in the physiological range of about 1 to 8.

More precisely, Eudragit RL is a poly(ethylacrylate, methylmethacrylate, trimethylammonioethyl methacrylate chloride) with a molar ratio of the monomer units of 1:2:0.2 and a molecular weight of 150,000. Eudragit RS is a poly(ethylacrylate, methylmethacrylate, trimethylammonioethyl methacrylate chloride) with a molar ratio of 1:2:0.1 and a molecular weight of 150,000.

According to a preferred embodiment of the present invention the methacrylic acid copolymers are selected from the group consisting of poly(ethylacrylate, methacrylic acid) and poly(ethylacrylate, methylmethacrylate, trimethylammonioethyl methacrylate chloride) copolymers.

Eudragit RL and RS are used in the art to form water insoluble film coats for sustained-release products. Eudragit RL films are more permeable than Eudragit RS. In the present invention, combination of high and low permeability copolymers is used to get film of varying permeability.

In a preferred embodiment of the present invention, the inner polymeric coating comprises of a mixture of a first copolymer, poly(ethylacrylate, methylmethacrylate, trimethylammonioethyl methacrylate chloride) with a molar ratio of 1:2:0.2 and a molecular weight of 150,000 and a second copolymer, a poly(ethylacrylate, methylmethacrylate, trimethylammonioethyl methacrylate chloride) with a molar ratio of 1:2:0.1 and a molecular weight of 150,000; the ratio of said second copolymer to said first copolymer being in the range of 1:1 to 1:10 and more preferably in the range of 1:1 to 1:8, respectively. The film coating prepared by using both these polymers provides pH independent release of cefuroxime axetil. This inner polymeric coating is essential to achieve sustained-release of the active ingredient over a period of time.

In a preferred embodiment of the present invention, the outer polymeric coating comprises of poly(ethylacrylate, methacrylic acid) with a molar ratio of 1:1 and average molecular weight around 250,000, a film forming acrylic resin polymer that controls the release of drug at the pH of stomach. This outer enteric polymeric coating is provided to control the initial rapid release of drug in the acidic environment. As the pH increases gradually, the entire coating is dissolved and drug release rate is increased, and to control the release of the drug hereafter, an inner coating of pH independent polymers is used.

In a still preferred embodiment of the present invention, the inner acrylic coating is derived from a mixture of two acrylic resin lacquers used in the form of aqueous dispersions, commercially available from Rohm Pharma under the Tradename Eudragit RL 30 D and Eudragit RS 30 D and the outer acrylic coating is derived from aqueous acrylate dispersion, commercially available from Rohm Pharma under the Tradename Eudragit L 30 D-55. These copolymers will be present in the composition at a concentration in the range of about 0.1% to about 15% by weight of controlled release form each.

The Eudragit RL/RS dispersions may be mixed together in a desired ratio in order to finally obtain a controlled release cefuroxime formulation having a desirable dissolution profile. The dissolution profile of a composition prepared according to present invention may be adjusted to a desired rate by changing the relative amounts of different acrylic lacquers included in the coating.

The polymeric aqueous dispersions used for coating may also contain additives such as plasticizers. Plasticizers are used to assist in the film forming characteristics of the polymeric coating and for providing greater integrity and elasticity to the film coats. Examples of plasticizers that may be employed in the coatings of this invention are triethyl citrate, triacetin, diethyl phthalate, lanolin, mineral oil, glycerol, polyethylene glycol, propylene glycol and chlorobutanol. The preferred plasticizer is trietyl citrate.

The amount of plasticizer present in the aqueous dispersion may be from 1% to 20% by weight of dry polymer. Preferably, the plasticizer will be present in an amount of from about 1% to about 10% by weight of the dry polymer.

In an attempt to develop a sustained controlled release composition, trials have been conducted by using Eudragit polymers mentioned above alone or in combination with each other. The results obtained on use of 15% w/w of Eudragit RS 30 D (i); 12% w/w of Eudragit RL 30 D (ii); 12% w/w of Eudragit L 30 D-55 (iii); 2 and 8% w/w of (i) and (ii); 1, 5 and 4% w/w of [(i+ii)+iii]; and 0.5, 2.5 and 4% w/w of [(i+ii)+iii] respectively, of controlled release form, are summarized in Table 1 and graphically represented in FIG. 1.

Figure 1:
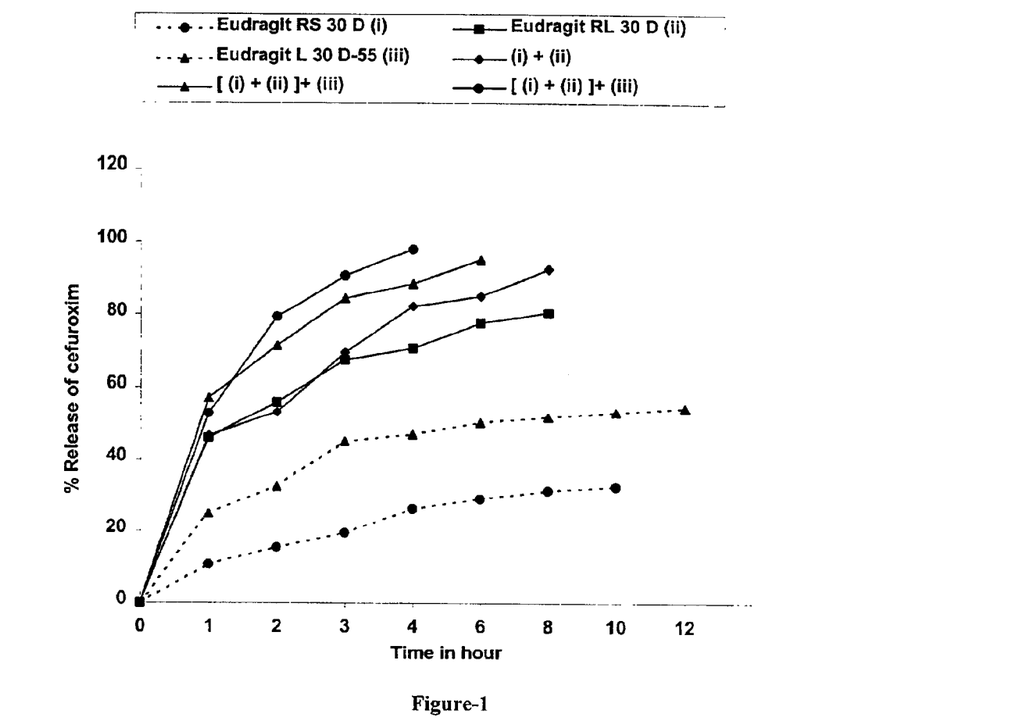
FIG. 1 is a graph illustrating the dissolution profile of cefuroxime when Eudragit RS 30 D, Eudragit RL 30 D, Eudragit L 30 D-55 are used alone or in combination with each other.

When Eudragit RS 30 D was used alone it was observed that the drug release was slow in the acidic pH as well as in the alkaline pH. The release profile did not vary much with change in the concentration of Eudragit RS 30 D. Since Eudragit RL 30 D is more permeable than Eudragit RS 30 D, Eudragit RL 30 D was used alone to check the release profile. Here the initial release was fast in the acidic pH but it was retarded than desired at the later stage. To achieve desired drug release profile further trials were taken with the use of enteric polymer Eudragit L 30 D-55 to optimize the release at initial stage and using a combination of pH independent polymers Eudragit RS 30 D and Eudragit RL 30 D to sustain the release at later stage. The combination of pH dependent and pH independent copolymers is essential to overcome the limitations associated with their use, when used alone. The eudragit polymers used are manufactured by Rohm Pharma GmbH Westerstadt, West Germany.

TABLE 1

| | | % Release of the active | | | | | |
|---|---|---|---|---|---|---|---|
| Time in hour | Conventional/ without polymer | Eudragit RS 30 D alone (i) | Eudragit RL 30 D alone (ii) | Eudragit L 30 D-55 alone (iii) | (i) + (ii) | [(i + ii)] + (iii) | [(i + ii)] + (iii) |
| 1 | 100 | 10.7 | 46.2 | 25.1 | 46.6 | 57.2 | 52.9 |
| 2 | | 15.4 | 56.0 | 32.5 | 53.2 | 71.4 | 79.4 |
| 3 | | 19.5 | 67.5 | 45.2 | 69.5 | 84.6 | 90.8 |
| 4 | | 26.4 | 70.7 | 47.1 | 82.4 | 88.6 | 98.0 |
| 6 | | 29.0 | 77.6 | 50.3 | 85.2 | 95.0 | |
| 8 | | 31.2 | 80.6 | 51.8 | 92.5 | | |
| 10 | | 32.4 | | 53.3 | | | |
| 12 | | | | 54.6 | | | |

In a preferred embodiment of the present invention the ratio of inner coating to outer coating is in the range of 1:0.3 to 1:5.

In a more preferred embodiment of the present invention the ratio of inner coating to outer coating is in the range of 1:0.5 to 1:4.

In a preferred embodiment of the present invention, the controlled release form of the pharmaceutical composition comprises from about 30% to about 80% by weight of cefuroxime axetil and about 1% to about 30% by weight of a mixture of methacrylic acid copolymers a) and b), wherein individual copolymers are present in the composition at a concentration in the range of about 0.1% to about 15% by weight of controlled release form.

In a more preferred embodiment of the present invention, the controlled release form of the ceutical composition comprises from about 30% to about 80% by weight of cefuroxime and about 1% to about 25% by weight of a mixture of methacrylic acid copolymers a) and b), wherein the inner polymeric coat comprises from about 1% to about 12% by weight and the outer polymeric coat comprises from about 2% to about 10% by weight of controlled release form.

In a most preferred embodiment of the present invention, the controlled release form of the pharmaceutical composition comprises from about 30% to about 80% by weight of cefuroxime axetil and about 1% to about 20% by weight of a mixture of methacrylic acid copolymers a) and b) wherein the inner polymeric coat comprises from about 1% to about 9% by weight and the outer polymeric coat comprises from about 2% to about 8% by weight of controlled release form.

In another preferred embodiment of the present invention the inner coating comprises a mixture of poly(ethylacrylate, methylmethacrylate, trimethylammonioethyl methacrylate chloride) with a molar ratio of 1:2:0.2 and a molecular weight of 150,000 in the range of about 1% to about 8% and a poly(ethylacrylate, methylmethacrylate, trimethylammonioethyl methacrylate chloride) with a molar ratio of 1:2:0.1 and a molecular weight of 150,000 in the range of about 0.1% to about 5% by weight of controlled release form.

In another preferred embodiment of the present invention, the outer polymeric coating comprises of poly(ethylacrylate, methacrylic acid) with a molar ratio of 1:1 and average molecular weight around 250,000 in the range of about 2% to about 10% by weight of controlled release form.

In yet another preferred embodiment of the present invention, the outer polymeric coating comprises of poly (ethylacrylate, methacrylic acid) with a molar ratio of 1:1 and average molecular weight around 250,000 in the range of about 2% to about 8% by weight of controlled release form.

According to the present invention the pharmaceutical composition may contain probenecid in controlled release or immediate release form in an amount from about 250 mg to about 1000 mg.

According to present invention the pharmaceutical composition may contain one or more of pharmaceutically acceptable excipients in an amount of about 1% to about 25% by weight of the total weight of the composition. These excipients may be water soluble or water dispersible diluents. Examples of water soluble diluents that maybe used in the present invention include lactose, mannitol, glucose, sorbitol, maltose, dextrates, dextrins and the like. Water dispersible diluent refers to insoluble pharmaceutical excipients, which disperse readily in water such as microcrystalline cellulose, starch, pre-gelatinized starch, magnesium aluminum silicates and the like.

Preferably the controlled release form of the composition contains pharmaceutically acceptable water dispersible diluents in the range from about 5% to about 25% by weight.

According to present invention the pharmaceutical composition may also contain a suitable water soluble or water dispersible binder in an amount from about 1% to about 5% by weight of total composition. Examples of water soluble binders that may be used include acacia, dextrins, gelatin, liquid glucose, maltodextrin, polyvinyl pyrrolidone, polyethylene oxide and the like. Examples of water dispersible binders that may be used include methylcellulose, carboxymethylcellulose, hydroxypropylcellulose and the like. The preferred binder is polyvinyl pyrrolidone.

According to present invention the pharmaceutical composition may also contain tablet lubricants, at a concentration in the range of about 0.1% to 5% by weight either alone or in combination of total weight of the composition. The lubricants that may be used include talc, stearic acid, magnesium stearate, colloidal silicon dioxide, calcium stearate, zinc stearate, hydrogenated vegetable oil, polyethylene glycol, mineral oil and the like. Preferably the lubricant is selected from talc, stearic acid, magnesium stearate, colloidal silicon dioxide and hydrogenated vegetable oil.

The controlled release form of the present invention contains wetting agent at a concentration in the range from about 0.1% to about 4% by weight. Preferably the wetting agent is sodium lauryl sulphate.

The controlled release composition of the present invention is formulated such that it rapidly disintegrates into controlled release coated granules. The composition of the present invention may contain disintegrant in the range from about 1% to about 25% by weight, preferably from about 1% to about 20% by weight of the total composition. The disintegrant may be selected from sodium starch glycolate, crosslinked polyvinyl pyrrolidone, potato starch, defatted soyabean extract, crosslinked carboxymethyl cellulose sodium, in which croscarmellose sodium being particularly preferred.

The immediate release probenecid part of the composition is prepared by mixing probenecid and one or more water soluble or water dispersible diluents and the blend is granulated by compaction or by wet granulation with a suitable binder, followed by sieving and the granules obtained are lubricated. The fines incorporated in the blend form about 10% to about 30% by weight, preferably from about 10% to about 20%.

Alternately, probenecid may be present as controlled release form, prepared by mixing probenecid with water dispersible diluent, and granulated by wet granulation with a suitable binder or compaction to obtain granules. The resulting granules are sized and then coated by methacrylate coatings by using wet granulation technique or fluid bed processor to obtain coated probenecid granules.

The controlled release granules of the composition are prepared by blending together cefuroxime axetil and suitable excipients, followed by compaction (for example, roller compaction) to give sheets or direct compression to give slugs or wet granulation with a suitable binder for e.g. polyvinyl pyrrolidone. The granules are produced by breaking down the compacted slugs or sheets, achieved by passing it through a sieve or on oscillating granulator. The coating of the granules may be achieved by wet granulation with methacrylates in a planatory mixer or by using fluid bed processor.

The coating of granules by wet granulation process consists of wet granulating the precompacted and sized blend consisting of cefuroxime axetil and suitable pharmaceutical excipients using the aqueous dispersions of low and high permeability pH independent Eudragits for e.g. Eudragit RS 30 D and Eudragit RL 30 D in a planatory mixer. The wet mass is passed through 10 mesh and dried. These granules are further granulated using aqueous dispersion of enteric Eudragits for e.g. Eudragit L 30 D-55. The wet mass is passed through 10 mesh and dried. The controlled release coated granules obtained are sized, blended with immediate release or controlled release probenecid granules for composition containing probenecid. The blend may be further lubricated before being compressed into a tablet. For composition without probenecid the controlled release coated granules of cefuroxime axetil may be blended with excipients and lubricants before being compressed into a tablet. The fines incorporated in the blend are from about 10% to about 30% by weight of controlled release form and for probenecid part from about 10% to 20%. The fines denote a fraction having a size less than 250 microns. The granules are compressed into a single monolithic tablet or a bilayered tablet.

Alternately, the coated granules may be prepared by particulate coating in fluid bed processor. The precompacted and sized blend consisting of cefuroxime axetil and suitable pharmaceutical excipients is coated in fluid bed processor. The temperature of the inlet and outlet air of fluid bed processor should be maintained between 40° C. to 65° C. and 20° C. to 40° C., respectively. The preferred inlet and outlet air temperatures are between 55° C. to 65° C. and 30° C. to 40° C., respectively. The air rate is adjusted such that the particles are maintained in a suspended state and the fluidized bed is at desired temperature. The aqueous dispersions of low and high permeability pH independent Eudragits for e.g. Eudragit RS 30 D and Eudragit RL 30 D is sprayed onto the fluidized particles at a rate optimum to provide complete coating of particles and dried. The dried granules are further coated using aqueous dispersion of enteric Eudragit for e.g. Eudragit L 30 D-55. The controlled release coated granules obtained are sized, lubricated and blended with immediate release or controlled release probenecid granules for composition containing probenecid. For composition without probenecid the controlled release coated granules of cefuroxime axetil may be blended with excipients and lubricants before being compressed into a tablet. The fines incorporated in the blend are from about 10% to about 30% by weight of controlled release form and for probenecid part from about 10% to 20%. The fines denote a fraction having a size less than 250 microns. The granules are compressed into single monolithic tablets or bi-layered tablets.

Preferably, at least 80% of the granules before coating are in the size range of about 650 to about 850 microns and not less than 70% of the coated granules fall in the size range of about 650 microns to about 850 microns.

The cefuroxime axetil incorporated into the compositions will preferably be in the amorphous form.

The controlled release formulation prepared according to present invention may be administered once daily. The effective therapeutic once daily dose of cefuroxime that can be administered by compositions of present invention is 1 g cefuroxime alone or 1 g cefuroxime and 1 g probenecid.

Figure 2:
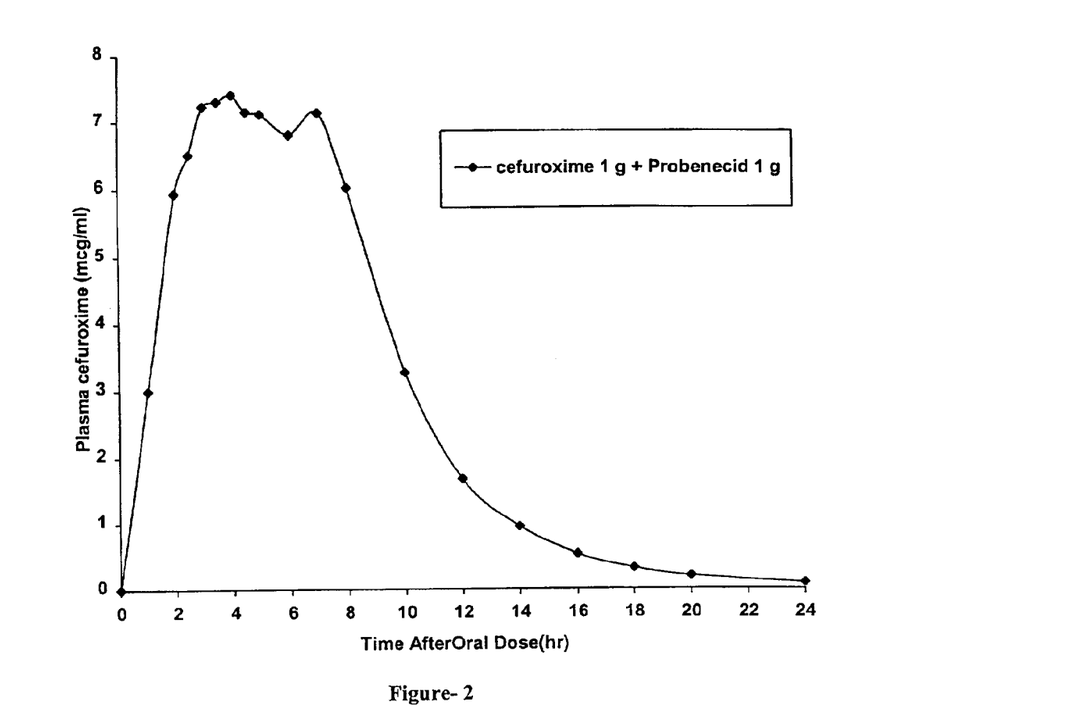
FIG. 2 is a graph illustrating the release over time of cefuroxime into the bloodstream for a composition of the present invention containing probenecid.

In-vivo study was conducted to test the bioavailability of cefuroxime axetil compositions prepared according to present invention, under fed condition on eight healthy human volunteers. FIG. 2 shows the results obtained as the linear plot of mean plasma concentration of cefuroxime V/s time in hour for a composition containing probenecid. It could be seen that effective plasma concentration of cefuroxime is maintained over 16 hours when composition of the invention containing probenecid was administered to human volunteers.

Figure 3:
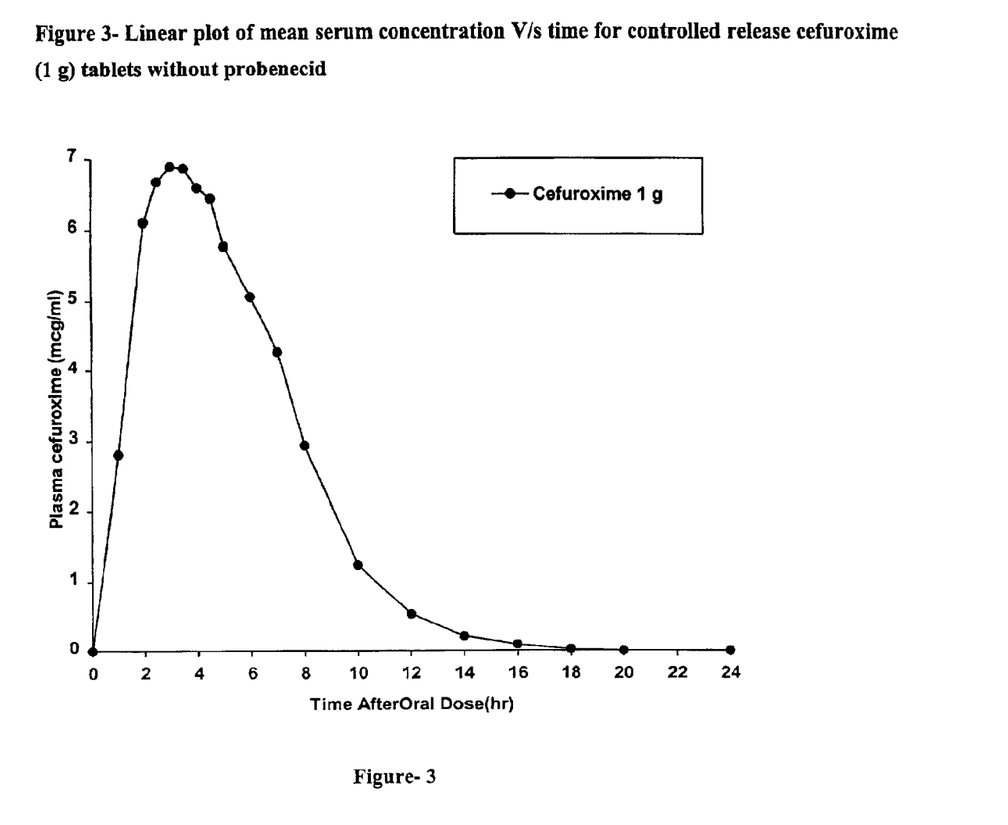
FIG. 3 is a graph illustrating the release over time of cefuroxime into the bloodstream for a composition of the present invention without probenecid.

FIG. 3 shows the results obtained as the linear plot of mean plasma concentration of cefuroxime V/s time in hour for a composition without probenecid. It could be seen that effective plasma concentration of cefuroxime is maintained over 12 hours when composition of the invention not containing probenecid was administered to human volunteers. Thus this demonstrates that the composition developed with or without probenecid, both meet the requirement of once daily dosage regime.

It has been reported (Craig W A, Diagn. Microbiol. Infect. Dis., 25,213, 1996) for lactam antibiotics that bacteriologic efficacy of 90–100% is achieved when T/MIC is 40–50% of dosing interval or higher. In some cases the T/MIC of as low as 30% is also effective.

For compositions of the present invention without probenecid T/MIC is 33% and that with probenecid is 43%. The T/MIC for a composition without probenecid is comparable to that of conventional cefuroxime and for a composition with probenecid the values are superior.

Although the formulations with and without probenecid comply to a once a day criteria, the formulation with probenecid has better efficacy.

The present invention is illustrated by the following examples. Examples are not intended to be limiting to the scope of the invention.

EXAMPLES

The tablets exemplified in examples 1 to 5 given below were tested for cefuroxime release in 900 ml of 0.07 N hydrochloric acid for 1 hour after which the dissolution media was changed to pH 6.8 phosphate buffer (USP apparatus type II) and were rotated at 75 rpm. Further fresh samples were analysed for probenecid release using 900 ml of 6.8 pH phosphate buffer using USP apparatus type II at 75 rpm. The dissolution results are given in respective tables for each example.

Tablets Containing Probenecid

Procedure for Example 1 and 2

Components 1) to 3) were screened through a 40 mesh sieve. The blend obtained was lubricated using hydrogenated vegetable oil and compacted using roller compactor. The slugs obtained were sized and used for coating by methacrylates by wet granulation or in fluid bed processor to obtain coated granules.

Components 8) to 10) were screened through a 30 mesh sieve and compacted on roller compactor and sized. Both the granules were mixed, remaining excipients were added, lubricated and compressed into tablets.

Example 1

| Ingredients | Weight (mg/tablet) | % w/w |
|---|---|---|
| Controlled Release Form | | |
| 1) Cefuroxime Axetil | 601.97 | 72.00 |
| 2) Microcrystalline Cellulose | 100.00 | 12.00 |
| 3) Sodium Lauryl Sulphate | 4.52 | 0.54 |
| 4) Hydrogenated Vegetable Oil | 6.00 | 0.71 |
| 5) Eudragit RS 30 D | 14.00 | 1.67 |
| 6) Eudragit RL 30 D | 56.00 | 6.70 |
| 7) Eudragit L 30 D-55 | 53.90 | 6.44 |

-continued

Immediate release form

| | | Weight (mg/tablet) | % w/w |
|---|---|---|---|
| 8) | Probenecid | 500.00 | 65.07 |
| 9) | Microcrystalline Cellulose | 70.61 | 9.18 |
| 10) | Croscarmellose Sodium | 20.40 | 2.65 |
| 11) | Hydrogenated Vegetable Oil | 9.00 | 1.17 |
| 12) | Microcrystalline Cellulose | 18.33 | 2.38 |
| 13) | Colloidal Silicon Dioxide | 24.00 | 3.12 |
| 14) | Sodium Lauryl Sulphate | 5.00 | 0.65 |
| 15) | Croscarmellose Sodium | 115.00 | 15.00 |
| 16) | Hydrogenated Vegetable Oil | 6.00 | 0.78 |

| Time (hour) | Percent Cefuroxime Released (%) |
|---|---|
| 1 | 39.9 |
| 2 | 50.0 |
| 3 | 73.1 |
| 4 | 80.5 |
| 6 | 87.9 |
| 8 | 91.4 |

| Time (min) | Percent Probenecid Released (%) |
|---|---|
| 10 | 95.4 |
| 20 | 99.2 |
| 30 | 100.2 |

Example 2

| | Ingredients | Weight (mg/tablet) | % w/w |
|---|---|---|---|
| Controlled Release Form | | | |
| 1) | Cefuroxime Axetil | 613.50 | 78.10 |
| 2) | Microcrystalline Cellulose | 88.60 | 11.28 |
| 3) | Sodium Lauryl Sulphate | 4.52 | 0.57 |
| 4) | Hydrogenated Vegetable Oil | 6.00 | 0.76 |
| 5) | Eudragit RS 30 D | 7.12 | 0.90 |
| 6) | Eudragit RL 30 D | 35.60 | 4.53 |
| 7) | Eudragit L 30 D-55 | 30.21 | 3.84 |
| Immediate release form | | | |
| 8) | Probenecid | 500.00 | 69.01 |
| 9) | Microcrystalline Cellulose | 76.00 | 10.50 |
| 10) | Croscarmellose Sodium | 10.00 | 1.40 |
| 11) | Hydrogenated Vegetable Oil | 4.00 | 0.55 |
| 12) | Microcrystalline Cellulose | 18.00 | 2.50 |
| 13) | Colloidal Silicon Dioxide | 30.00 | 4.14 |
| 14) | Sodium Lauryl Sulphate | 5.00 | 0.70 |
| 15) | Croscarmellose Sodium | 75.45 | 10.40 |
| 16) | Hydrogenated Vegetable Oil | 6.00 | 0.80 |

| Time (hour) | Percent Cefuroxime Released (%) |
|---|---|
| 1 | 57.0 |
| 2 | 71.0 |
| 3 | 84.6 |
| 4 | 88.6 |
| 6 | 95.0 |

| Time (min) | Percent Probenecid Released (%) |
|---|---|
| 10 | 88.2 |
| 20 | 95.3 |
| 30 | 101.6 |

Example 3

Components 1) to 3) were screened through a 40 mesh sieve. The blend obtained was lubricated using hydrogenated vegetable oil and compacted using roller compactor. The slugs obtained were sized and used for coating by methacrylates.

Component 8) and 9) were screened through 30 mesh sieve and granulated with polyvinyl pyrrolidone solution in isopropyl alcohol in planatary mixture. The granules were sized and mixed with controlled release cefuroxime axetil granules, remaining excipients were added, lubricated and further compressed into tablet.

| | Ingredients | Weight (mg/tablet) | % w/w |
|---|---|---|---|
| Controlled Release Form | | | |
| 1) | Cefuroxime Axetil | 611.24 | 79.6 |
| 2) | Microcrystalline Cellulose | 87.76 | 11.43 |
| 3) | Sodium Lauryl Sulphate | 5.00 | 0.65 |
| 4) | Hydrogenated Vegetable Oil | 6.00 | 0.78 |
| 5) | Eudragit RS 30 D | 3.55 | 0.46 |
| 6) | Eudragit RL 30 D | 17.75 | 2.31 |
| 7) | Eudragit L 30 D-55 | 36.56 | 4.76 |
| Immediate release form | | | |
| 8) | Probenecid | 500.00 | 71.21 |
| 9) | Starch | 50.00 | 7.12 |
| 10) | Polyvinyl pyrrolidone | 11.00 | 1.56 |
| 11) | Microcrystalline Cellulose | 30.14 | 4.29 |
| 12) | Colloidal Silicon Dioxide | 15.00 | 2.13 |
| 13) | Sodium Lauryl Sulphate | 6.00 | 0.85 |
| 14) | Croscarmellose Sodium | 80.00 | 11.40 |
| 15) | Hydrogenated Vegetable Oil | 10.00 | 1.42 |

| Time (hour) | Percent Cefuroxime Released (%) |
|---|---|
| 1 | 44.50 |
| 2 | 72.20 |
| 3 | 85.30 |
| 4 | 93.30 |

| Time (min) | Percent Probenecid Released (%) |
|---|---|
| 10 | 98.80 |
| 20 | 102.20 |
| 30 | 103.30 |

Example 4

Component 1) & 2) Were screened through a 40 mesh sieve the blend was granulated using a solution of sodium lauryl sulfate in water followed by a solution of polyvinyl pyrrolidone in water in a planatory mixer. The granules were sized and used for coating by methacrylates using triethyl citrate as a plasticizer, in a fluid bed processor to obtain coated granules.

Component 9) and 10) were screened through 30 mesh sieve and granulated with polyvinyl pyrrolidone solution in isopropyl alcohol in a planatary mixture The granules were sized and mixed with controlled release cefuroxime axetil granules, remaining excipients were added, lubricated and further compressed into tablet.

| | Ingredients | Weight (mg/tablet) | % w/w |
|---|---|---|---|
| Controlled Release Form | | | |
| 1) | Cefuroxime Axetil | 607.45 | 77.80 |
| 2) | Microcrystalline Cellulose | 96.46 | 12.35 |
| 3) | Sodium Lauryl Sulphate | 9.00 | 1.15 |
| 4) | Polyvinyl Pyrrolidone | 14.54 | 1.86 |
| 5) | Eudragit RS 30 D | 3.63 | 0.46 |
| 6) | Eudragit RL 30 D | 18.18 | 2.33 |

-continued

| | | | |
|---|---|---|---|
| 7) | Eudragit L 30 D-55 | 30.00 | 3.84 |
| 8) | Triethyl Citrate | 1.50 | 0.2 |
| Immediate release form | | | |
| 9) | Probenecid | 500.00 | 71.35 |
| 10) | Microcrystalline Cellulose | 50.00 | 7.13 |
| 11) | Polyvinyl pyrrolidone | 11.00 | 1.56 |
| 12) | Microcrystalline Cellulose | 28.74 | 4.10 |
| 13) | Colloidal Silicon Dioxide | 15.00 | 2.14 |
| 14) | Sodium Lauryl Sulphate | 6.00 | 0.85 |
| 14) | Croscarmellose Sodium | 80.00 | 11.40 |
| 15) | Hydrogenated Vegetable Oil | 10.00 | 1.42 |

| Time (hour) | Percent Cefuroxime Released (%) |
|---|---|
| 1 | 45.1 |
| 2 | 73.4 |
| 3 | 87.9 |
| 4 | 97.6 |

| Time (min) | Percent Probenecid Released (%) |
|---|---|
| 10 | 98.8 |
| 20 | 102.2 |
| 30 | 103.3 |

Example 5

Cefuroxime axetil and microcrystalline cellulose were screened through 40 mesh sieve. The blend was granulated using a solution of sodium lauryl sulphate in water, followed by a solution of polyvinyl pyrrolidone in water in a planatory mixer. The granules were sized and used for coating by methacrylates in a fluid bed processor to obtain coated granules.

Probenecid and microcrystalline cellulose were screened through 30 mesh sieve and granulated using a solution of polyvinyl pyrrolidone in isopropyl alcohol. The granules were sized and used for coating by methacrylates in a fluid bed processor.

The resulting granules of cefuroxime axetil and probenecid were mixed, remaining excipients were added, lubricated and further compressed into tablets.

| | Ingredients | Weight (mg/tablet) | % w/w |
|---|---|---|---|
| Controlled Release Form | | | |
| 1) | Cefuroxime Axetil | 611.24 | 39.43 |
| 2) | Microcrystalline Cellulose | 119.76 | 7.72 |
| 3) | Sodium Lauryl Sulphate | 11.00 | 0.71 |
| 4) | Polyvinyl Pyrrolidone | 37.50 | 2.42 |
| 5) | Eudragit RS 30 D | 46.00 | 2.97 |
| 6) | Eudragit RL 30 D | 60.42 | 3.90 |
| 7) | Eudragit L 30 D-55 | 62.0 | 4.0 |
| 8) | Probenecid | 500.00 | 32.25 |
| 9) | Croscarmellose Sodium | 77.00 | 4.96 |
| 10) | Colloidal Silicon Dioxide | 15.00 | 0.97 |
| 11) | Hydrogenated Vegetable Oil | 10.00 | 0.65 |

| Time (hour) | Percent Cefuroxime Released (%) | Percent Probenecid Released (%) |
|---|---|---|
| 1 | 52.9 | 58.2 |
| 2 | 79.4 | 75.8 |
| 3 | 90.8 | 86.5 |
| 4 | 98.0 | 91.6 |

Tablets Without Probenecid

Example 6

Components 1) to 3) were screened through a 40 mesh sieve. The blend obtained was lubricated using hydrogenated vegetable oil and compacted using roller compactor. The slugs obtained were sized and used for coating by methacrylates to obtain coated granules. These granules were mixed with remaining excipients, lubricated and compressed into tablets.

The tablets were tested for cefuroxime release in 900 ml of 0.07 N hydrochloric acid for 1 hour, after which the dissolution medium was changed to pH 6.8 phosphate buffer (USP apparatus Type II, 75 rpm).

| | Ingredients | Weight (mg/tablet) | % w/w |
|---|---|---|---|
| Controlled Release Form | | | |
| 1) | Cefuroxime Axetil | 607.53 | 65.32 |
| 2) | Microcrystalline Cellulose | 94.53 | 10.16 |
| 3) | Sodium Lauryl Sulphate | 4.52 | 0.48 |
| 4) | Hydrogenated Vegetable Oil | 6.00 | 0.64 |
| 5) | Eudragit RS 30 D | 3.56 | 0.38 |
| 6) | Eudragit RL 30 D | 25.00 | 2.68 |
| 7) | Eudragit L 30 D-55 | 51.81 | 5.57 |
| 8) | Microcrystalline Cellulose | 46.00 | 5.00 |
| 9) | Colloidal Silicon Dioxide | 30.00 | 3.22 |
| 10) | Sodium Lauryl Sulphate | 6.00 | 0.64 |
| 11) | Croscarmellose Sodium | 50.00 | 5.37 |
| 12) | Hydrogenated Vegetable Oil | 5.00 | 0.53 |

| Time (hour) | Percent Cefuroxime Released (%) |
|---|---|
| 1 | 34.6 |
| 2 | 44.3 |
| 3 | 67.4 |
| 4 | 83.7 |
| 6 | 96.1 |

Example 7

Component 1) and 2) were screened through 40 mesh sieve, the blend was granulated using a solution of sodium lauryl sulphate in water, followed by a solution of polyvinyl pyrrolidone in water in a planatory mixer. The granules were sized and coated by methacrylates in a fluid bed processor to obtain coated granules. These granules were mixed with remaining excipients, lubricated and compressed into tablets.

The tablets were tested for cefuroxime release in 900 ml of 0.07 N hydrochloric acid for 1 hour, after which the dissolution medium was changed to pH 6.8 phosphate buffer (USP apparatus Type II, 75 rpm).

| | Ingredients | Weight (mg/tablet) | % w/w |
|---|---|---|---|
| Controlled Release Form | | | |
| 1) | Cefuroxime Axetil | 611.24 | 65.72 |
| 2) | Microcrystalline Cellulose | 87.76 | 9.43 |
| 3) | Sodium Lauryl Sulphate | 5.00 | 0.53 |
| 4) | Polyvinyl Pyrrolidone | 21.12 | 2.27 |
| 5) | Eudragit RS 30 D | 3.62 | 0.39 |
| 6) | Eudragit RL 30 D | 18.12 | 2.00 |
| 7) | Eudragit L 30 D-55 | 29.87 | 3.21 |

-continued

| | | | |
|---|---|---|---|
| 8) | Microcrystalline Cellulose | 62.12 | 6.68 |
| 9) | Colloidal Silicon Dioxide | 30.00 | 3.22 |
| 10) | Sodium Lauryl Sulphate | 6.00 | 0.65 |
| 11) | Croscarmellose Sodium | 50.00 | 5.37 |
| 12) | Hydrogenated Vegetable Oil | 5.00 | 0.53 |

| Time (hour) | Percent Cefuroxime Released (%) |
|---|---|
| 1 | 48.6 |
| 2 | 71.8 |
| 3 | 82.1 |
| 4 | 88.7 |

What is claimed is:

1. A fast disintegrating controlled release oral composition comprising a core material containing cefuroxime axetil present as controlled release form, and optionally probenecid, said controlled release form comprising
    a) an outer coating of a polymer selected from aqueous dispersions of enteric methacrylic acid and methacrylic acid esters anionic copolymers having carboxygroup as the functional group or mixtures thereof and;
    b) an inner coating of a sustained-release copolymer selected from aqueous dispersions of acrylate and methacrylate pH independent, neutral copolymers having quaternary ammonium group as a functional group or mixtures thereof; said composition releases cefuroxime axetil in amounts of more than 80% in 4 hours and the outer coating controls the initial rapid release of cefuroxime axetil from the composition.

2. A composition as claimed in claim 1 wherein probenecid is present as controlled release form.

3. A composition as claimed in claim 1 containing from about 30% to about 80% of cefuroxime axetil by weight of controlled release form.

4. A composition as claimed in claim 1 containing cefuroxime axetil in an amount which is equivalent to cefuroxime from 250 mg to 1500 mg.

5. A composition as claimed in claim 1 wherein cefuroxime axetil is essentially amorphous.

6. A composition as claimed in claim 1 wherein a) and b) are present in an amount from about 1% to about 30% by weight comprising from about 0.1% to about 15% of each copolymer present in the composition, by weight of controlled release form.

7. A composition as claimed in claim 1, wherein the outer enteric coating comprises a poly(ethylacrylate, methacrylic acid) with a molar ratio of 1:1 and average molecular weight around 250,000.

8. A composition as claimed in claim 1, wherein the inner coating comprises a mixture of a first copolymer, poly(ethylacrylate, methylmethacrylate, trimethylammonioethyl methacrylate chloride) with a molar ratio of 1:2:0.2 and a molecular weight of 150,000 and a second copolymer, a poly(ethylacrylate, methylmethacrylate, trimethylammonioethyl methacrylate chloride) with a molar ratio of 1:2:0.1 and a molecular weight of 150,000.

9. A composition as claimed in claim 1, wherein the ratio of inner coating to outer coating is in the range of 1:0.3 to 1:5.

10. A composition as claimed in claim 1, wherein the ratio of inner coating to outer coating is in the range of 1:0.5 to 1:4.

11. A composition as claimed in claim 8, wherein the first copolymer of the inner coating comprises a poly (ethylacrylate, methylmethacrylate, trimethylammonioethyl methacrylate chloride) with a molar ratio of 1:2:0.2 and a molecular weight of 150,000 in the range of about 1% to about 8% by weight of controlled release form.

12. A composition as claimed in claim 8, wherein the second copolymer of the inner coating comprises a poly (ethylacrylate, methylmethacrylate, trimethylammonioethyl methacrylate chloride) with a molar ratio of 1:2:0.1 and a molecular weight of 150,000 in the range of about 0.1% to about 5% by weight of controlled release form.

13. A composition as claimed in claim 8, wherein the inner coating comprises a mixture of a first copolymer, poly(ethylacrylate, methylmethacrylate, trimethylammonioethyl methacrylate chloride) with a molar ratio of 1:2:0.2 and a molecular weight of 150,000 and a second copolymer, a poly(ethylacrylate, methylmethacrylate, trimethylammonioethyl methacrylate chloride) with a molar ratio of 1:2:0.1 and a molecular weight of 150,000; the ratio of said second copolymer-to said first copolymer being in the range of 1:1 to 1:10.

14. A composition as claimed in claim 8, wherein the inner coating comprises a mixture of a first copolymer, poly(ethylacrylate, methylmethacrylate, trimethylammonioethyl methacrylate chloride) with a molar ratio of 1:2:0.2 and a molecular weight of 150,000 and a second copolymer, a polycethylacrylate, methylmethacrylate, trimethylammonioethyl methacrylate chloride) with a molar ratio of 1:2:0.1 and a molecular weight of 150,000; the ratio of said second copolymer to said first copolymer being in the range of 1:1 to 1:8.

15. A composition as claimed in claim 1 wherein the outer coating comprises from about 2% to about 10% by weight of controlled release form.

16. A composition as claimed in claim 1 wherein the outer coating comprises from about 2 to about 8% by weight of controlled release form.

17. A composition as claimed in claim 1 wherein the inner coating comprises from about 1 to about 12% by weight of controlled release form.

18. A composition as claimed in claim 1 wherein the inner coating comprises from about 1 to about 9% by weight of controlled release form.

19. A composition as claimed in claim 1, wherein the total dry polymeric content is about 5 to about 30% by weight of the controlled release form.

20. A composition as claimed in claim 1, wherein the controlled release form comprises from about 30% to about 80% by weight of cefuroxime axetil and about 1% to about 25% by weight of a mixture of a) and b) wherein the inner polymeric coat comprises from about 1% to about 12% by weight and the outer polymeric coat comprises from about 2% to about 10% by weight of controlled release form.

21. A composition as claimed in claim 1, wherein the controlled release form comprises from about 30% to about 80% by weight of cefuroxime axetil and about 1% to about 20% by weight of a mixture of a) and b) wherein the inner polymeric coat comprises from about 1% to about 9% by weight and the outer polymeric coat comprises from about 2% to about 8% by weight of controlled release form.

22. A composition as claimed in claim 1 containing probenecid in an amount from 250 mg to 1000 mg.

23. A composition as claimed in claim 1, which further contains at least one water soluble or water dispersible diluent.

24. A composition as claimed in claim 23, wherein the water soluble or water dispersible diluent comprises about 1% to about 25% by weight of the composition.

25. A composition as claimed in claim 23, wherein the water dispersible diluent comprises about 5% to about 25% by weight of the controlled release form.

26. A composition as claimed in claim 25, wherein the water dispersible diluent is microcrystalline cellulose.

27. A composition as claimed in claim 1, which further contains a wetting agent in amount from about 0.1% to about 4% by weight of controlled release form.

28. A composition as claimed in claim 27 wherein the wetting agent is sodium lauryl sulphate.

29. A composition as claimed in claim 1, which further contains a lubricant in an amount from about 0.1% to about 5% of the composition.

30. A composition as claimed in claim 29 wherein the lubricant is hydrogenated vegetable oil.

31. A composition as claimed in claim 1, which further contains a disintegrant in amount from about 1% to about 25% by weight of the composition.

32. A composition as claimed in claim 31, wherein the disintegrant is cross linked carboxymethyl cellulose sodium.

33. A composition as claimed in claim 1, which further contains a binder in amount from about 1% to about 5% by weight of the composition.

34. A composition as claimed in claim 33, wherein the binder is polyvinyl pyrrolidone.

35. A composition as claimed in claim 1, wherein the inner coating contains a plasticizer.

36. A composition as claimed in claim 1, wherein the outer coating contains a plasticizer.

37. A composition as claimed in claim 35, wherein the plasticizer is present in an amount of from about 1% to about 20% by weight of dry polymer.

38. A composition as claimed in claim 37, wherein the plasticizer is triethyl citrate.

39. A process for preparing a fast disintegrating controlled release oral composition containing cefuroxime axetil as controlled release form and optionally probenicid as claimed in claim 1, which comprises spraying onto a fluidized bed of cefuroxime axetil core material an aqueous dispersion of an inner polymeric coating, retrieving and drying the coated core material and applying to a fluidized bed of the dried material an aqueous dispersion of an outer polymeric coating material and drying the coated particles wherein the inner polymeric coating is a mixture of a first copolymer, poly(ethylacrylate, methylmethacrylate, trimethylammonioethyl methacrylate chloride) with a molar ratio of 1:2:0.2 and a molecular weight of 150,000 and a second copolymer, a poly(ethylacrylate, methylmethacrylate, trimethylammonioethyl methacrylate chloride) with a molar ratio of 1:2:0.1 and a molecular weight of 150,000; and the outer polymeric coating is a poly(ethylacrylate, methacrylic acid) with a molar ratio of 1:1 and average molecular weight around 250,000, wherein the first copolymer of inner coating is present in amount of about 1 to about 8%, the second copolymer of inner coating is present in amount of about 0.1 to about 5% and outer coating is present in amount of about 2% to about 10% by weight of controlled release form, respectively.

40. The process according to claim 39 wherein the inner polymeric coating optionally contains a plasticizer, and further wherein the outer polymeric coating optionally contains a plasticizer.

41. A process for the preparation of a pharmaceutical composition as claimed in claim 1 comprising mixing together cefuroxime axetil, diluents and wetting agent to form a blend, further compacting or wet granulating, sizing and coating the granules by wet granulation or coating in fluidized bed processor using copolymers a) and b), further drying, sizing, lubricating the granules and compressing to form monolithic tablets or bilayered tablets.

42. A process for the preparation of a pharmaceutical composition as claimed in claim 1 comprising mixing together cefuroxime axetil, diluents and wetting agent to form a blend, further compacting or wet granulating, sizing and coating the granules by wet granulation or coating in fluidized bed processor using copolymers a) and b), further drying, sizing, lubricating the granules and compressing into tablets along with immediate release probenecid granules to form monolithic tablets or bilayered tablets.

43. A process for the preparation of pharmaceutical composition as claimed in claim 1 comprising mixing together probenecid, diluent and disintegrant together, compacting or wet granulating, sizing and coating the granules by wet granulation or coating in fluidized bed processor using copolymers a) and b), further drying, sizing, lubricating the granules and compressing into tablets along with coated controlled release cefuroxime axetil granules to form monolithic tablets or bilayered tablets.

44. A process for the preparation of pharmaceutical composition as claimed in claim 1 comprising mixing together probenecid, diluent and disintegrant together, compacting or wet granulating, sizing and blending with lubricant and compressing the blend into tablets along with controlled release coated granules of cefuroxime axetil to form monolithic tablets or bilayered tablets.

45. A process for the preparation of a pharmaceutical composition as claimed in claim 39 wherein the inlet and outlet air temperatures of fluid bedprocessor are maintained between 40° C. to 65° C. and 20° C. to 40° C., respectively.

46. A process for the preparation of a pharmaceutical composition as claimed in claim 39 wherein the inlet and outlet air temperatures of fluid bed processor are maintained between 55° C. to 65° C. and 30° C. to 40° C., respectively.

47. A composition as claimed in claim 7, wherein the ratio of inner coating to outer coating is in the range of 1:0.3 to 1:5.

48. A composition as claimed in claim 8, wherein the ratio of inner coating to outer coating is in the range of 1:0.3 to 1:5.

49. A composition as claimed in claim 7, wherein the ratio of inner coating to outer coating is in the range of 1:0.5 to 1:4.

50. A composition as claimed in claim 8, wherein the ratio of inner coating to outer coating is in the range of 1:0.5 to 1:4.

51. A composition as claimed in claim 7, wherein the controlled release form comprises from about 30% to about 80% by weight of cefuroxime axetil and about 1% to about 25% by weight of a mixture of a) and b) wherein the inner polymeric coat comprises from about 1% to about 12% by weight and the outer polymeric coat comprises from about 2% to about 10% by weight of controlled release form.

52. A composition as claimed in claim 8, wherein the controlled release form comprises from about 30% to about 80% by weight of cefuroxime axetil and about 1% to about 25% by weight of a mixture of a) and b) wherein the inner polymeric coat comprises from about 1% to about 12% by weight and the outer polymeric coat comprises from about 2% to about 10% by weight of controlled release form.

53. Composition as claimed in claim 7, wherein the controlled release form comprises from about 30% to about 80% by weight of cefuroxime axetil and about 1% to about 20% by weight of a mixture of a) and b) wherein the inner polymeric coat comprises from about 1% to about 9% by weight and the outer polymeric coat comprises from about 2% to about 8% by weight of controlled release form.

54. A composition as claimed in claim 8, wherein the controlled release form comprises from about 30% to about 80% by weight of cefuroxime axetil and about 1% to about 20% by weight of a mixture of a) and b) wherein the inner polymeric coat comprises from about 1% to about 9% by weight and the outer polymeric coat comprises from about 2% to about 8% by weight of controlled release form.

55. A composition as claimed in claim 36, wherein the plasticizer is present in an amount of from about 1% to about 20% by weight of dry polymer.

56. A composition as claimed in claim 55, wherein the plasticizer is triethyl citrate.

57. A process for the preparation of a pharmaceutical composition as claimed in claim 41, wherein the inlet and outlet air temperatures of fluid bed processor are maintained between 40° C. to 65° C. and 20° C. to 40° C., respectively.

58. A process for the preparation of a pharmaceutical composition as claimed in claim 42, wherein the inlet and outlet air temperatures of fluid bed processor are maintained between 40° C. to 65° C. and 20° C. to 40° C., respectively.

59. A process for the preparation of a pharmaceutical composition as claimed in claim 43, wherein tile inlet and outlet air temperatures of fluid bed processor are maintained between 40° C. to 65° C. and 20° C. to 40° C., respectively.

60. A process for the preparation of a pharmaceutical composition as claimed in claim 41, wherein the inlet and outlet air temperatures of fluid bed processor are maintained between 55° C. to 65° C. and 30° C. to 40° C. respectively.

61. A process for the preparation of a pharmaceutical composition as claimed in claim 42, wherein the inlet and outlet air temperatures of fluid bed processor are maintained between 55° C. to 65° C. and 30° C. to 40° C. respectively.

62. A process for the preparation of a pharmaceutical composition as claimed in claim 43, wherein the inlet and outlet air temperatures of fluid bed processor are maintained between 55° C. to 65° C. and 30° C. to 40° C. respectively.

63. A fast disintegrating controlled release oral composition comprising a core material containing cefuroxime axetil present as controlled release form, and probenecid, said controlled release form comprising a) an outer coating of a polymer selected from aqueous dispersions of enteric methacrylic acid and methacrylic acid esters anionic copolymers having carboxygroup as the functional group or mixtures thereof and;

b) an inner coating of a sustained-release copolymer selected from aqueous dispersions of acrylate and methacrylate pH independent, neutral copolymers having quaternary ammonium group as a functional group or mixtures thereof; said composition releases cefuroxime axetil in amounts of more than 80% in 4 hours and the outer coating controls the initial rapid release of cefuroxime axetil from the composition.

64. A process for preparing a fast disintegrating controlled release oral composition containing cefuroxime axetil as controlled release form and probenicid as claimed in claim 1, which comprises spraying onto a fluidized bed of cefuroxime axetil core material an aqueous dispersion of an inner polymeric coating, retrieving and drying the coated core material and applying to a fluidized bed of the dried material an aqueous dispersion of an outer polymeric coating material and drying the coated particles wherein the inner polymeric coating is a mixture of a first copolymer, poly(ethylacrylate, methylmethacrylate, trimethylammonioethyl methacrylate chloride) with a molar ratio of 1:2:0.2 and a molecular weight of 150,000 and a second copolymer, a poly(ethylacrylate, methylmethacrylate, trimethylammonioethyl methacrylate chloride) with a molar ratio of 1:2:0.1 and a molecular weight of 150,000; and the outer polymeric coating is a poly(ethylacrylate, methacrylic acid) with a molar ratio of 1:1 and average molecular weight around 250,000, wherein the first copolymer of inner coating is present in amount of about 1 to about 8%, the second copolymer of inner coating is present in amount of about 0.1 to about 5% and outer coating is present in amount of about 2% to about 10% by weight of controlled release form, respectively.

* * * * *